United States Patent
Higa

(10) Patent No.: US 7,745,202 B2
(45) Date of Patent: Jun. 29, 2010

(54) DETERGENT MADE USE OF FERMENTATION TECHNOLOGY AND PRODUCTION METHOD THEREOF

(75) Inventor: Teruo Higa, Ginowan (JP)

(73) Assignee: EM Research Organization, Inc., Uruma-Shi (JP)

( * ) Notice: Subject to any disclaimer, the term of this patent is extended or adjusted under 35 U.S.C. 154(b) by 674 days.

(21) Appl. No.: 10/589,795

(22) PCT Filed: Feb. 18, 2005

(86) PCT No.: PCT/JP2005/002637

§ 371 (c)(1),
(2), (4) Date: Aug. 17, 2006

(87) PCT Pub. No.: WO2005/080539

PCT Pub. Date: Sep. 1, 2005

(65) Prior Publication Data

US 2007/0190625 A1    Aug. 16, 2007

(30) Foreign Application Priority Data

Feb. 20, 2004    (JP) ................ 2004-045518

(51) Int. Cl.
*C11D 3/12* (2006.01)
*C11D 13/00* (2006.01)
*C12P 7/64* (2006.01)
*C12P 39/00* (2006.01)

(52) U.S. Cl. .............. 435/264; 435/42; 435/134; 510/108; 510/507

(58) Field of Classification Search .............. None
See application file for complete search history.

(56) References Cited

U.S. PATENT DOCUMENTS 2,539,889 A * 1/1951 Bradford ............... 554/157
5,602,065 A * 2/1997 Higa .................. 501/141
5,863,882 A 1/1999 Lin et al.
6,649,397 B1 11/2003 Nakamura

FOREIGN PATENT DOCUMENTS

| EP | 0 245 560 | 11/1987 |
|---|---|---|
| EP | 1 178 108 | 2/2002 |
| JP | 08-196265 A1 | 8/1996 |
| JP | 08-245992 A1 | 9/1996 |
| JP | 08-252086 A1 | 10/1996 |
| JP | 2000-302619 | 10/2000 |
| JP | 2000-302619 A1 | 10/2000 |
| JP | 2001-026796 A1 | 1/2001 |
| JP | 2001-032000 A1 | 2/2001 |
| JP | 2001-115200 A1 | 4/2001 |
| JP | 2002-226893 A1 | 8/2002 |
| JP | 2003145144 A * | 5/2003 |
| WO | 99/57243 A1 | 11/1999 |
| WO | 03/002704 | 1/2003 |
| WO | 03/104376 | 12/2003 |

\* cited by examiner

Primary Examiner—Taeyoon Kim
(74) Attorney, Agent, or Firm—Burr & Brown

(57) ABSTRACT

A process for producing soap is provided, which includes effective microorganisms (EM) and EM-X ceramic powder, which are added to enhance the degree of saponification of fat, strengthen the cleaning power, and to provide a detergent that is capable of proliferating effective microorganisms in sewage water after washing and cleaning the sewage water, and which exhibits an effect as a water purification material after washing. Effective microorganisms (EM) including mainly facultative anaerobic lactic acid bacteria, yeast and photosynthetic bacteria and EM-X ceramic powder are added in the process of producing the soap, thereby, the treated material obtained according to the present invention exhibits an environmental purification effect as a substrate of benign microorganisms or a microorganism material.

3 Claims, 1 Drawing Sheet

Flow chart of production method of solid form soap

Flow chart of production method of liquid soap

DETERGENT MADE USE OF FERMENTATION TECHNOLOGY AND PRODUCTION METHOD THEREOF

TECHNICAL FIELD

The present invention relates to a soap product which enhances the degree of saponification of fat and strengthens the cleaning power by adding effective microorganisms (EM) and EM-X ceramic powder in a production process of soap, and which proliferates effective microorganisms in sewage water after washing for cleaning the sewage water.

BACKGROUND ART

The conventional water treatment has employed a method for collecting sewage in cleaning equipment or a sewage treatment plant for treating sewage. However, household miscellaneous wastewater contributes largely to pollution. Household miscellaneous waste water contains various substances. Among them, there is concern that detergents could provide an adverse affect on the ecological system. In particular, various surfactants contained in synthetic detergents remarkably harm the existence of bacteria and protozoa used as a main body in a sewage treatment technique, which lowers the treatment capacity and leads a vicious circle of increase in pollution. Moreover, in a final process of sewage treatment, many chlorine-type bactericides are used, thus the influence on the ecological system becomes serious.

Considering that the household miscellaneous waste water including surfactants lowers the treatment capacity of the sewage treatment plant and chlorine-type bactericides are being used, it can be said that an intermediate treatment process in the sewage treatment plant would not be sufficient as a basic solution.

Recently, the accumulation of the above problems causes serious pollution of rivers and oceans, and recovery has been tried at an expensive cost. However, these problems remain unsolved, and become more serious. In such situations, people's attention has been drawn to soap that is decomposed by natural microorganisms, and a public movement to use soap made from waste oil has been growing. However, when soap has a low saponification degree and an insufficient cleaning power, it is apparent that water quality is deteriorated in accordance with the increase of soap usage.

Patent reference 1: Japanese Unexamined Patent Publication 2002-226893

Patent reference 2: Japanese Unexamined Patent Publication 2002-128683

SUMMARY OF THE INVENTION

An object of the present invention is to reduce soap usage by enhancing the degree of saponification of fat and strengthen its cleaning power, so that the pollution process from sewage water is fundamentally disconnected. In other words, the present invention is characterized in that a soap product with an enhanced degree of saponification is produced by adding effective microorganisms (EM), which are effective for water purification, and using EM-X ceramic powder as a catalyst.

In the production of the soap of the present invention, the following are added:

effective microorganisms (EM), mainly consisting of lactic acid bacteria, yeast and photosynthetic bacteria (EM: trademark of EM Research Organization Inc.) among anaerobe effective microorganisms as effective microorganisms (EM); and ceramic powder (EM-X ceramic: manufactured by EM Sogonet Co., Ltd., Amron Co., Ltd.) which is prepared by mixing a condensed liquid of antioxidant substances produced by effective microorganisms (EM) (EM-X: manufactured by Tropical Plant Resources Research Institute; trademark of EM Research Organization Inc.) and EM in a clay, aging, and baking at 800-1200° C.

The soap product thus produced enhances the degree of saponification, includes functionality and an effective component of microorganisms, and exhibits an effect as a water purification material after washing.

The present invention is characterized in that, on selecting microorganisms, in particular, effective microorganisms (EM) are introduced in a production process of soap as a living organism playing a starter role in an environmental purification process. EM mainly consists of facultative anaerobic lactic acid bacteria, yeast and photosynthetic bacteria. In the present invention, by introducing EM particularly before and after the saponification process in the soap product production, the soap product obtained according to the present invention exhibits an environmental purification effect as a substrate of benign microorganism or a microorganism material.

Ordinarily, the decomposition of organisms discharged to environment starts in an artificial purification process conducted in purification equipment or a sewage treatment plant, and by a self-purification operation. However, by utilizing the soap product of the present invention, proliferation of benign microorganisms is accelerated immediately after use, and malign microorganisms that use the soap product and sewage water discharged in washing as a nutrient have no chance to proliferate.

Moreover, the present invention utilizes facultative anaerobic effective microorganisms. Basically, in environmental purification technologies, there are many cases using aerobic microorganisms. *Bacillus* genus is the typical example as described in Japanese Unexamined Patent Publication 2002-226893. Microorganisms composing an ecological system are roughly classified into two types; one is an aerobic microorganism, and the other is an anaerobic microorganism. It is said that aerobic microorganisms occupy almost all of the earth and anaerobic microorganisms occupy the very small portion. Anaerobic microorganisms themselves are classified into obligatory anaerobic bacteria and facultative bacteria. Obligatory anaerobic bacteria cannot live under coexistence with oxygen. On the other hand, facultative bacteria are susceptible to oxygen but are of a microorganism group having a metabolic system capable of growing even under existence of oxygen. Effective microorganisms (EM) used in the present invention is the latter bacteria group among anaerobic bacteria, which can act even under coexistence with oxygen.

The role of the foregoing facultative bacteria under an aerobic environment is as follows. Although mainly an active body under an aerobic environment is aerobic bacteria, facultative anaerobic bacteria work together in almost all the cases of the backgrounds. In addition, many facultative anaerobic bacteria have a wide environmental adjustability and independent alibility. Although the proliferation speed of facultative anaerobic bacteria is not as high as that of aerobic bacteria, the facultative anaerobic bacteria has a feature in that it proliferates irrespective of the influence of environmental factors. Moreover, many microorganisms are confirmed such that they contribute to the decomposition of persistent materials of which aerobic bacteria cannot realize the decomposition, they are particularly said to be an essential factor for environmental purification.

Then, in order to conduct environmental purification easily, effective microorganisms (EM) consisting mainly of lactic acid bacteria, yeast and photosynthetic bacteria group which are facultative anaerobes has been widely used. In the present invention, by compounding EM and EM-X ceramic powder in a detergent, a detergent is provided having an enhanced degree of saponification and cleaning power, and whereby the amount of the soap product used is reduced, the functionality and effective component of the microorganisms are contained, and the environmental load is small.

In other words, on the occasion of discharging the soap of the present invention into environment, effective microorganisms contained in the soap product naturally proliferate by utilizing sewage water discharged during the washing process as a nutrient in an early stage, and due to an effective component not contained in an ordinary detergent, the sorts of microorganism capable of employing the present soap as a nutrient increase, which contributes to the accelerated decomposition of soap itself. Further, when anaerobic bacteria are contained in the proliferated microorganisms, from the characteristic that respective anaerobic bacteria live together, various enzymes are produced in the decomposition process of organic matter. Furthermore, from a phenomenon called concurrent metabolism decomposing substances other than a target substance, they will contribute to the decomposition of environmental pollution causing substances other than the target.

As described above, the soap product obtained according to the present invention not only changes sewage water as an environmental pollution source to a purification source automatically, but also suppresses the proliferation of various bacteria, which leads to a secondary effect on the suppression of slippery touch in a sink or bath tab, and suppresses the generation of bad odor substances.

In addition, the soap product according to the present invention contains many effective substances produced in a fermentation process of organic matter by facultative anaerobic bacteria, therefore, users can obtain not only positive effects of effective components, but also an effect of returning indigenous microorganisms in the environment to a sound state due to the excellent activation capability of benign microorganisms.

On the other hand, fats as a raw material subjected to a fermentation treatment by effective microorganisms can be used as a raw material for soap products and detergents other than for soap, like shampoo and as a moisture retention agent, so that the application is not restricted to soap per se.

DETAILED DESCRIPTION OF THE INVENTION

Next, a soap in which effective microorganisms are added according to the present invention and its preparation method will be described in detail.

The term "effective microorganisms" in the context of the present invention means microorganisms used in food processing for working effectively for humans, and they are a group of effective microorganisms (EM) of compound culture mainly of lactic acid bacteria, yeast and photosynthetic bacteria which are generally recognized as safe bacteria. These have an effective fermentation pattern for humans as a metabolic form of organic matter. A typical example of the common type of the microorganisms includes EM-1 (trademark of EM Research Organization Inc.), which is used in the present invention. EM-X ceramic powder used as a catalyst so as to enhance the degree of saponification is commercially available one manufactured by EM Sogonet Co., Ltd. and Amron Co., Ltd.

Since the soap product of the present invention is directed to soap, Examples 1 to 3 describe an introduction method of soap production, but basically for the purpose of the addition as a raw material, it can be used for all kinds of detergents. However, for a synthetic detergent containing a strong surfactant that kills microorganisms, it would kill microbes and protozoa in environment even if effective microorganisms (EM) of the present invention have resistance properties thereto. Therefore, it is not desirable to add effective microorganisms (EM) and EM-X ceramic powder in expectation of their water purification.

Next, production methods will be described in detail.

Example 1

Figure 1:
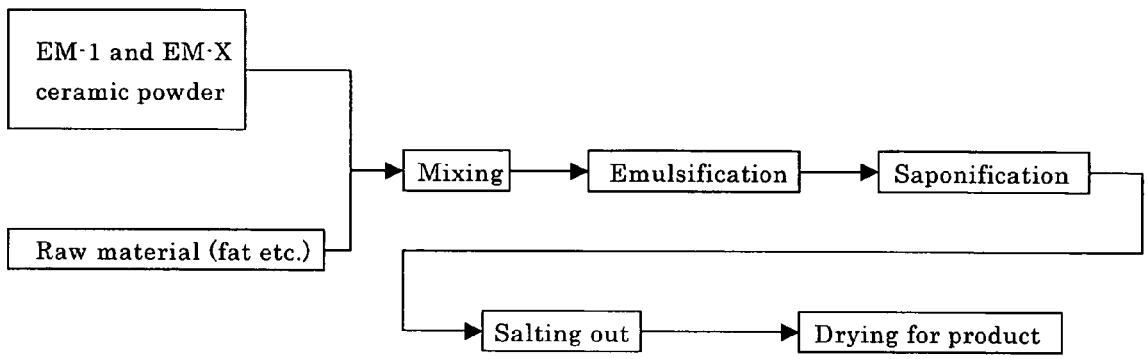
FIG. 1 is a flowchart of production method of solid form soap according to the present invention.

FIG. 1 is one example of flow chart of a method producing solid form soap, where during a pre-stage prior to an emulsification process, EM or a fermented material with EM, and EM-X ceramic powder are added to the raw material.

In this case, although the microorganisms added cannot be counted from soap as a viable cell, after using the soap product, the effective components contained therein become a nutrient for benign indigenous microorganisms present in environment, so that organic carbons in the soap product are rapidly decomposed.

The most simple production method is a method that EM-1 is added as a raw material, alternatively, a material fermented with EM can be used. An example of the fermented materials is aqueous fermented molasses or rice rinsed water. Also, extracts of various organics and various minerals can be directly added, but, before addition, fermentation by EM can afford the same effect as the addition of EM-1. Through the above processes, various fermentation substances can be added, and additives are studied according to the purpose of use. However, if all raw materials are treated by fermentation for addition, it is not realistic because time, space and cost saving are not obtained.

A basic production method is as follows. The effective results are obtained by replacement of EM-1 for all of water used, in consideration of cost, a sufficient effect can be obtained by addition of EM-1 and EM-X ceramic powder of 1%. In the case of compounding additives other than those, the amount is not required in exceeding EM-1 for addition.

Addition of EM-X ceramic powder is to enhance the degree of saponification by the catalytic activity. Table 1 shows the amount of soap portion formation depending on loadings of EM-X ceramic powder. As shown in Table 1, with increased in loads of EM-X ceramic powder, the amount of soap portion formation was increased.

TABLE 1

Influence of loadings of EM ceramic powder on the amount of soap portion formation

|  | No addition | 0.01% addition | 0.1% addition | 1% addition |
| --- | --- | --- | --- | --- |
| Cold water | 1.552 g | 1.449 g | 1.592 g | 1.642 g |
| Hot water | 1.446 g | 1.376 g | 1.489 g | 1.550 g |

Example 2

Figure 2:
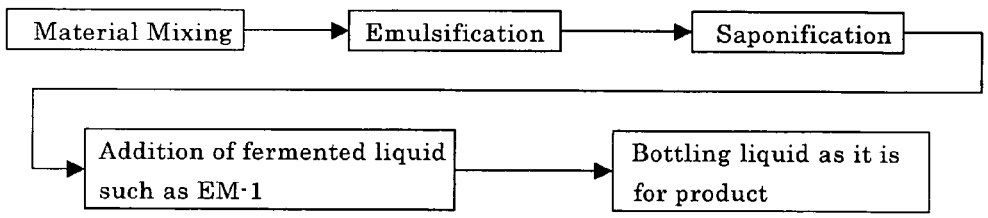
FIG. 2 is a flow chart of production method of liquid soap according to the present invention.

FIG. 2 is one example of a method for producing a liquid soap. After saponification, EM-1 or a secondary culture liquid of EM-1, or a fermented rice rinsed water, which is a high nutrition liquid can be added to produce a liquid soap. The treatment prior to the saponification step follows Example 1.

Table 2 is a table that the number of microorganisms contained in finished soap was counted. As shown in Table 2, when microorganisms are added after saponification, viable cell count is possible.

TABLE 2

Number of microorganisms in soap

| Sort | Yeast | Lactic acid bacteria |
| --- | --- | --- |
| Ordinary soap | Not detected | Not detected |
| EM added soap | $10 \times 10^4$ | $15 \times 10^4$ |

Example 3

Further, there are methods such as a direct fermentation method of raw materials and a method providing fat with antioxidant power by adding a fermented material to fat. Specifically, as described in Japanese Unexamined Patent Publication 2002-128683, a material that rice bran is fermented by EM is used. However, in Japanese Unexamined Patent Publication 2002-128683, aerobic microorganisms are used and utilized as an aqueous solution, but a primary object of the present invention is that hydrophobic antioxidant substances being present more than water-soluble antioxidant substances in a fermented product are integrated into fat. When raw materials are directly fermented, EM-1 will be used, on this occasion, acceleration of fermentation can be done by conducting monosaccharides like glucose as a substrate. Also, even without the addition of a substrate, by adding EM-1 or fermented substances generated in accordance with it, and setting an aging period of about 45-90 days, the fermentation treatment of raw material is possible.

Next, environmental purification effects will be described in detail.

Example 4

The soap product according to the present invention was added into a water tank whose bottom part was bedded with soil being filled with tap water. Table 3 shows that respective additive materials were added thereto, then, changes of turbidity were followed in time axis. As shown in Table 3, compared to a synthetic detergent or soap without EM, in the water tank that the soap product of the present invention was added, the lowering of turbidity was observed from 4 days afterward, and the results that a high transparent state was maintained long time were obtained.

TABLE 3

Influence of additive materials on turbidity [FAU]

| Additive | 4 days | 13 days | 20 days |
| --- | --- | --- | --- |
| No addition | 69.7 | 45.3 | 41.3 |
| Surfactant [synthetic detergent] | 44.0 | 37.3 | 39.3 |
| Soap | 24.0 | 28.7 | 40.0 |
| EM added soap | 14.0 | 20.7 | 26.7 |

INDUSTRIAL APPLICABILITY

As describe above, the present invention can contribute to the purification of global environment because, the addition of an effective microorganisms (EM) and EM-X ceramic powder during the production of the soap product enhances the degree of saponification of fat, strengthens the cleaning power, and facilitates the proliferation of effective microorganisms in sewage water after introducing the soap product into the sewage water.

The invention claimed is:

1. A method of producing a soap product comprising:
   providing facultative anaerobic effective microorganisms including at least lactic acid bacteria, yeast and photosynthetic bacteria or a fermented material containing facultative anaerobic effective microorganisms including at least lactic acid bacteria, yeast and photosynthetic bacteria;
   providing a ceramic powder catalyst by forming a mixture of a clay and a condensed liquid of an antioxidant substance produced by effective microorganisms to form a mixture, aging the mixture and baking the mixture;
   compounding the effective microorganisms and the ceramic powder catalyst and adding the compounded effective microorganisms and the ceramic powder to fats and mixing; and
   performing emulsification and saponification;
   wherein the ceramic powder catalyst enhances a degree of saponification of the fats during the production of the soap product; and
   wherein after the soap product is introduced into a waste water system, the effective microorganisms provided thereby proliferate in the waste water system to enhance a decomposition rate of the soap product itself as well as a decomposition rate of indigenous pollutants in the waste water system to accelerate water purification.

2. The method according to claim 1, wherein a hydrophobic antioxidant substance of the fermented material containing facultative anaerobic effective microorganisms in is integrated into the fats for direct fermentation thereof.

3. The method according to claim 1, further comprising a step of adding a fermented liquid containing a facultative anaerobic effective microorganisms including at least lactic acid bacteria, yeast and photosynthetic bacteria after the saponification step to provide a liquid soap product.

* * * * *